(12) United States Patent
Passerini et al.

(10) Patent No.: US 10,241,968 B2
(45) Date of Patent: Mar. 26, 2019

(54) SYSTEM AND METHOD FOR REAL-TIME SIMULATION OF PATIENT-SPECIFIC CARDIAC ELECTROPHYSIOLOGY INCLUDING THE EFFECT OF THE ELECTRICAL CONDUCTION SYSTEM OF THE HEART

(71) Applicant: Siemens Healthcare GmbH, Erlangen (DE)

(72) Inventors: Tiziano Passerini, Plainsboro, NJ (US); Tommaso Mansi, Princeton, NJ (US); Ali Kamen, Skillman, NJ (US); Bogdan Georgescu, Plainsboro, NJ (US); Saikiran Rapaka, Pennington, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 241 days.

(21) Appl. No.: 15/119,386

(22) PCT Filed: Feb. 17, 2015

(86) PCT No.: PCT/US2015/016126
§ 371 (c)(1),
(2) Date: Aug. 16, 2016

(87) PCT Pub. No.: WO2015/126815
PCT Pub. Date: Aug. 27, 2015

(65) Prior Publication Data
US 2017/0068796 A1    Mar. 9, 2017

Related U.S. Application Data

(60) Provisional application No. 61/940,935, filed on Feb. 18, 2014.

(51) Int. Cl.
*G06F 17/50*    (2006.01)
*G06F 17/11*    (2006.01)
(Continued)

(52) U.S. Cl.
CPC .............. *G06F 17/11* (2013.01); *A61B 34/10* (2016.02); *G06F 17/5009* (2013.01);
(Continued)

(58) Field of Classification Search
CPC ...... G06F 19/3437; G06F 19/00; G06F 17/11; G06F 17/5009; G16H 50/50; A61B 34/10; A61B 2034/105
(Continued)

(56) References Cited

U.S. PATENT DOCUMENTS

| 7,668,354 B2 | 2/2010 | O'Donnell et al. |
| 7,916,919 B2 | 3/2011 | Zheng et al. |

(Continued)

FOREIGN PATENT DOCUMENTS

| CN | 101043855 A | 9/2007 |
| CN | 101695442 A | 4/2010 |

(Continued)

OTHER PUBLICATIONS

H. Sermesant, H. Delingette, N. Ayache, "An Electromechanical Model of the Heart for Image Analysis and Simulation" IEEE Transactions on Medical Imaging, vol. 25, No. 5, May 2006, pp. 612-625.*

(Continued)

*Primary Examiner* — Dwin M Craig

(57) ABSTRACT

A method and system for simulating patient-specific cardiac electrophysiology including the effect of the electrical conduction system of the heart is disclosed. A patient-specific anatomical heart model is generated from cardiac image data of a patient. The electrical conduction system of the heart of (Continued)

the patient is modeled by determining electrical diffusivity values of cardiac tissue based on a distance of the cardiac tissue from the endocardium. A distance field from the endocardium surface is calculated with sub-grid accuracy using a nested-level set approach. Cardiac electrophysiology for the patient is simulated using a cardiac electrophysiology model with the electrical diffusivity values determined to model the Purkinje network of the patient.

46 Claims, 5 Drawing Sheets

(51) Int. Cl.
    *A61B 34/10*     (2016.01)
    *G16H 50/50*     (2018.01)
    *G06F 19/00*     (2018.01)

(52) U.S. Cl.
    CPC .............. *G06F 19/00* (2013.01); *G16H 50/50* (2018.01); *A61B 2034/105* (2016.02)

(58) Field of Classification Search
    USPC .......................................................... 703/2
    See application file for complete search history.

(56) References Cited

U.S. PATENT DOCUMENTS

| | | |
|---|---|---|
| 2008/0024488 A1 | 1/2008 | Visser et al. |
| 2010/0040272 A1 | 2/2010 | Zheng et al. |
| 2012/0022843 A1* | 1/2012 | Ionasec .................... G06T 13/20 703/9 |
| 2012/0232386 A1 | 9/2012 | Mansi et al. |
| 2013/0216110 A1 | 8/2013 | Zheng et al. |
| 2013/0226542 A1 | 8/2013 | Rapaka et al. |
| 2014/0022250 A1 | 1/2014 | Mansi et al. |
| 2015/0042646 A1 | 2/2015 | Comaniciu et al. |

FOREIGN PATENT DOCUMENTS

| | | |
|---|---|---|
| CN | 101782943 A | 7/2010 |
| CN | 102346811 A | 2/2012 |
| WO | WO2012109618 A2 | 8/2012 |

OTHER PUBLICATIONS

Sermesant, et al.; "An electromechanical model of the heart for image analysis and simulation", IEEE Transactions on Medical Imaging vol. 25, No. 5, pp. 612-625, XP001545798 / Jan. 5, 2006.
Roger, V. L., Go, A. S., Lloyd-Jones, D. M., Benjamin, E. J., Berry, J. D., Borden, W. B., . . . & Fullerton, H. J. (2012). Heart disease and stroke statistics—2012 update: a report from the American Heart Association. Circulation, 125(1), e2-e220.
McMurray, et al.; "ESC Guidelines for the diagnosis and treatment of acute and chronic heart failure 2012: The Task Force for the Diagnosis and Treatment of Acute and Chronic Heart Failure 2012 of the European Society of Cardiology. Developed in collaboration with the Heart Failure Association (HFA) of the ESC." European heart journal 33, No. 14 (2012): 1787-1847.
Daubert, J.-C. et. al.: "2012 EHRA/HRS expert consensus statement on cardiac resynchronization therapy in heart failure: implant and follow-up recommendations and management", in: Europace, vol. 14, No. 9, pp. 1236-1286, 2012.
Auricchio, Angelo, and Frits W. Prinzen. "Non-responders to cardiac resynchronization therapy." Circulation Journal 75.3 (2011): 521-527.
Tusscher, et al. "Modelling of the ventricular conduction system." Progress in biophysics and molecular biology 96.1-3 (2008): 152-170.
Rawling, D. A., Joyner, R. W., & Overholt, E. D. (1985). Variations in the functional electrical coupling between the subendocardial Purkinje and ventricular layers of the canine left ventricle. Circulation Research, 57(2), 252-261.
Ijiri, Takashi, et al. "A procedural method for modeling the purkinje fibers of the heart." The journal of physiological sciences 58.7 (2008): 481-486.
Sebastian, R., Zimmerman, V., Romero, D., & Frangi, A. F. (2011). Construction of a computational anatomical model of the peripheral cardiac conduction system. IEEE Transactions on Biomedical Engineering, 58(12), 3479-3482.
Vigmond, et al. "Effect of bundle branch block on cardiac output: a whole heart simulation study." Progress in biophysics and molecular biology 97.2-3 (2008): 520-542.
Colli Franzone, et al.; "Spread of excitation in 3-D models of the anisotropic cardiac tissue. II. Effects of fiber architecture and ventricular geometry." 1998; Mathematical Biosciences.
Kerckhoffs, et al. "Timing of depolarization and contraction in the paced canine left ventricle." Journal of cardiovascular electrophysiology 14.s10 (2003).
Sermesant, et al.; An anisotropic multi-front fast marching method for real-time simulation of cardiac electrophysiology; Jun. 2007; In International Conference on Functional Imaging and Modeling of the Heart (pp. 160-169). Springer, Berlin, Heidelberg.
Talbot, et al.; "Towards real-time computation of cardiac electrophysiology for training simulator." International Workshop on Statistical Atlases and Computational Models of the Heart. Springer, Berlin, Heidelberg, 2012.
Office Action dated Jun. 1, 2018 in corresponding Chinese patent application No. 201580009323.X.
Mitchell et al., "A Two-Current Model for the Dynamics of Cardiac Membrane", Bulletin of Mathematical Biology, 65 (5):767-793, 2003.
Ten Tusscher, et al., "Cell Model for Efficient Simulation of Wave Propagation in Human Ventricular Tissue Under Normal and Pathological Conditions", Physics in Medicine and Biology, 51, pp. 6141, 2006.

* cited by examiner

SYSTEM AND METHOD FOR REAL-TIME SIMULATION OF PATIENT-SPECIFIC CARDIAC ELECTROPHYSIOLOGY INCLUDING THE EFFECT OF THE ELECTRICAL CONDUCTION SYSTEM OF THE HEART

This application is a national stage (under 35 U.S.C. 371) of International Patent Application No. PCT/US2015/016126, filed Feb. 17, 2015, claiming the benefit of U.S. Provisional Application No. 61/940,935, filed Feb. 18, 2014, the disclosure of which is herein incorporated by reference in its entirety.

BACKGROUND OF THE INVENTION

The present invention relates to simulating cardiac electrophysiology of a patient, and more particularly to patient-specific simulation of cardiac electrophysiology of a patient including the effect of the electrical conduction system of the heart for planning or guidance of electrophysiology interventions.

The prevalence of heart rhythm disease is increasing in Western countries. While primary treatments are based on drugs, minimally invasive electrophysiology (EP) therapies are becoming effective enough to be considered as viable alternatives. For example, the use of ablative therapies is increasing for treatment of cardiac arrhythmias, such as atrial fibrillation or ventricular tachycardia, while Cardiac Resynchronization Therapy (CRT) is becoming a treatment of choice for heart failure patients. However, these therapies require thorough patient selection and complex planning, and their long term efficacy is still sub-optimal. Accordingly, tools and techniques to improve patient selection, therapy planning, and interventional guidance are desirable.

Computational models for real-time simulation of cardiac EP could be used for intra-operatory guidance and optimization of an EP intervention, as well as for reducing the duration of such procedures and thus reducing patient stress, especially in the case of invasive procedures. Unfortunately, a trade-off between model accuracy and computational cost is still a challenge, and no solution has been proposed to realize real-time modeling of the patient-specific electrophysiology including the electrical conduction system of the heart.

BRIEF SUMMARY OF THE INVENTION

The present invention provides a method and system for interactive patient-specific simulation of cardiac electrophysiology (EP) including the effect of the electrical conduction system of the heart from medical image data of a patient. Embodiments of the present invention provide an accurate patient-specific EP model that models the effect of the high speed conducting tissues (i.e., the Purkinje system) in the heart. Embodiments of the present invention reproduce the effect of high speed conducting tissue on the propagation of the electrical signal in the heart by correcting the numerical solution produced by EP solvers based on Cartesian grids, such that effect of the high speed conducting tissue can be modeled with an accuracy that does not depend of the grid spatial resolution. This allows real-time numerical solutions using a coarse grid for patient-specific modeling of cardiac EP including the effect of the high speed conducting system of the heart. Embodiments of the present invention provide both pre-operative intervention planning and intra-operative intervention guidance using real-time patient-specific cardiac EP simulations.

In one embodiment, a patient-specific anatomical heart model is generated from cardiac image data of a patient. Physical properties of cardiac tissue in the patient-specific anatomical heart model are modeled based on a distance of the cardiac tissue from one or more anatomical structures in the patient-specific anatomical heart model. Cardiac function for the patient is simulated using a cardiac model with the physical properties modeling based on the distance of the cardiac tissue from the one or more anatomical structures in the patient-specific anatomical heart model.

In one embodiment, the electrical conduction system of the heart of the patient is modeled by determining electrical properties of the cardiac tissue based on a distance of the cardiac tissue from the endocardium in the patient-specific anatomical heart model, and cardiac electrophysiology of the patient is simulated using a cardiac electrophysiology model with the electrical properties of the cardiac tissue determined to model the electrical conduction system of the heart of the patient.

These and other advantages of the invention will be apparent to those of ordinary skill in the art by reference to the following detailed description and the accompanying drawings.

DETAILED DESCRIPTION

The present invention relates to patient-specific simulation of cardiac electrophysiology (EP) including the effect of the electrical conduction system of the heart using medical imaging data of a patient. Embodiments of the present invention are described herein to give a visual understanding of the methods for patient-specific modeling and electrophysiology simulation using medical imaging data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
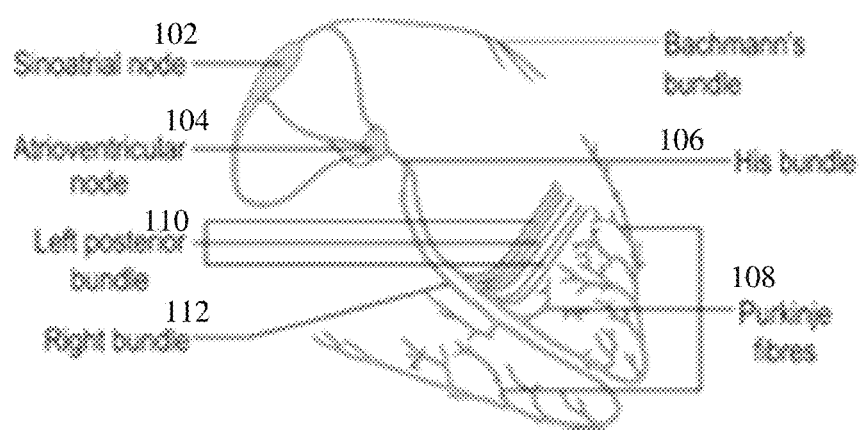
FIG. 1 illustrates the electrophysiological conduction system of the heart.

FIG. 1 illustrates the electrical conduction system of the heart. As shown in FIG. 1, the electrical conduction system of the heart is composed of several elements including: sinoatrial node 102, atrioventricular node 104, His bundle 106, and Purkinje fibers 108. In normal physiological conditions, the electrical pulse is spontaneously generated in the sinoatrial node 102—the natural pacemaker—localized at the junction of the superior vena cava with the right atrium. As the electrical wave propagates towards the atrioventricular node 104, the electrical wave depolarizes the atrial myocytes, which contract and pump the blood to the ventricles. After depolarization of the atria, the action potential reaches the atrioventricular (AV) node 104, localized in the lower part of the right atrium on the fibrous atrioventricular ring. The electrical impulse is then stopped for a few milliseconds to synchronize the heart. This "pause" is fundamental as it enables the atria to fully contract and completely pump the blood into the ventricles. Fibrous tissue separates the musculature of atria and ventricula, the only connection being the muscular bundle of His 106 departing from the AV node 104. After crossing the atrioventricular junction, the bundle of His 106 splits (usually in two branches) at the summit of the ventricular septum. The left bundle branch 110 is a series of fascicles spreading over the septum of the left ventricle and connecting with ordinary myocardial fibers. The right bundle branch 112 tends to remain a bundle until it reaches the anterior papillary muscle, where it splits in fascicles spreading over the right ventricle myocardium. The tree-like terminal branchings of the left and right bundles 110 and 112 are called Purkinje fibers 108 and extend subendocardially up to ⅓ or ½ of the ventricular thickness.

The His-Purkinje system is involved in abnormal excitation patterns that may lead to arrhythmias. Examples of this phenomenon include left or right branch blocks that cause delayed ventricle contraction, bundle branch reentry that is associated with tachycardia, and subendocardial focal activity considered to be of Purkinje origin that may result in tachycardia or fibrillation. Since the His-Purkinje system plays such an important role in both normal ventricular excitation and life threatening ventricular arrhythmias, modeling of the His-Purkinje system is important for a realistic ventricle model of the heart.

Early studies suggest the network of Purkinje fibers is densely diffused in the subendocardium, and that it connects to the ventricular muscle in discrete regions call Purkinje fiber-ventricle muscle (PV) junctions. Computational models have been developed to try to reproduce the tree-like structure of the Purkinje network and to capture peculiar features of the high speed conducting system, such as retrograde propagation. This feature may play a role in complex scenarios such as cardiac resynchronization therapy, in which pacing electrodes may be placed in areas of the myocardium that are reached by the distal termination of the Purkinje fibers. Current imaging techniques do not allow the detection of the heart conduction system in vivo, therefore anatomically detailed models of the Purkinje network cannot be directly validated. Such models are typically based on anatomical information from histological studies and personalized to correctly reproduce sites of earliest activation and normal activation sequence from electrical mapping studies. However, such models fall short of demonstrating real-time computational performance.

Various techniques have been proposed for the development of fast solvers for electrophysiology simulation. Such techniques include the use of Eikonal models to compute the arrival time of the depolarization wave without computing the action potential itself. Based on graph algorithms, Eikonal models are very efficient from a computational point of view. However, their extreme simplification makes them unfit to model complex structures such as the Purkinje system. Finite-element based models for electrophysiology simulation have been pushed to almost real-time performance, by tuning the model parameters to allow for coarser time and space discretization. However, the issue of accurate modeling of the effect of high-speed conduction tissue has not been addressed.

Embodiments of the present invention address the clinical need for real-time patient-specific cardiac EP computational models by providing accurate simulation of cardiac EP including the effect of the electrical conduction system of the heart on coarse computational grids. Embodiments of the present invention utilize the Lattice Boltzmann method for Electrophysiology (LBM-EP) to provide real-time or near real-time simulation of cardiac electrophysiology together with a method for the quantification of cardiac electrical diffusivity with sub-grid accuracy. In order to mimic the fast propagation of electrical waves along the electrical conduction system of the heart while keeping the computational problem tractable, embodiments of the present invention implement a "macro-scale" model, assuming that the electrical conduction fibers are evenly distributed in the subendocardial region. In the framework of EP solvers based on Cartesian computational grids (such as LBM-EP), grid cells corresponding to the electrical conduction fibers are assigned a high diffusion coefficient, function of the distance of the myocardial tissue from the endocardium. A grid-independent representation of the electrical conduction system is obtained by defining a rule to classify the myocardial tissue as part of the high speed bundles based on a sub-grid accurate evaluation of its distance from the endocardium. This allows for the use of coarse grids for the computation of patient electrophysiology while still achieving sub-grid resolution accuracy for modeling the effect of the electrical conduction system of the heart.

Embodiments of the present invention provide a method for patient-specific simulation of cardiac function, in which a patient-specific anatomical heart model is generated from cardiac image data of a patient, physical properties of cardiac tissue in the patient-specific anatomical heart are modeled model based on a distance of the cardiac tissue from one or more anatomical structures in the patient-specific anatomical heart model, and cardiac function for the patient is simulated using a cardiac model with the physical properties modeling based on the distance of the cardiac tissue from the one or more anatomical structures in the patient-specific anatomical heart model.

Figure 2:
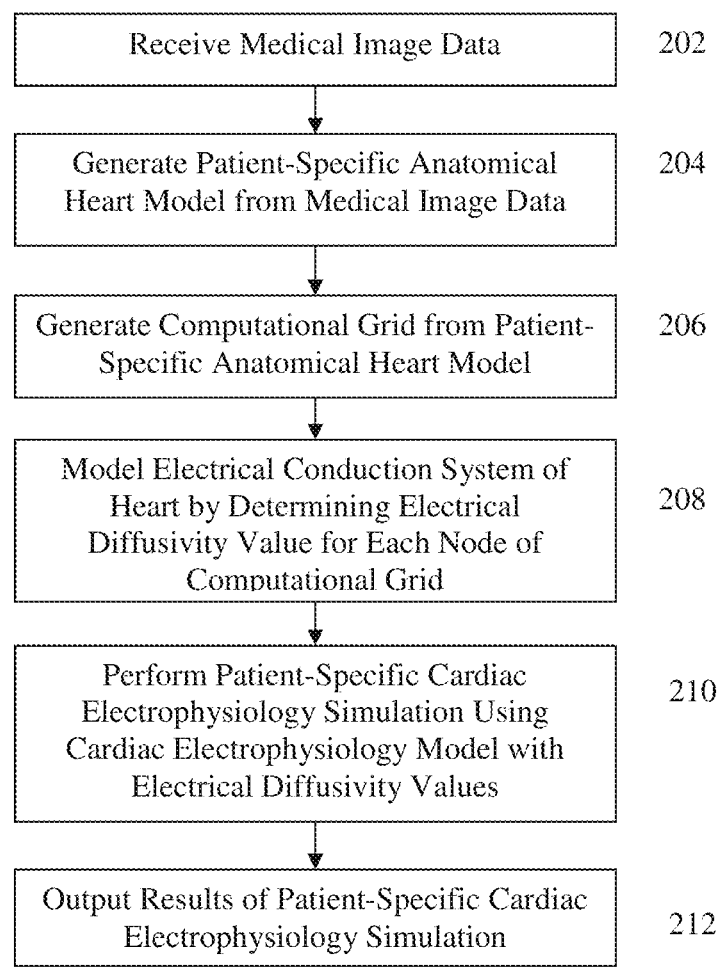
FIG. 2 illustrates a method for simulating patient-specific cardiac EP including the effect of the Purkinje system according to an embodiment of the present invention.

FIG. 2 illustrates a method for simulating patient-specific cardiac EP including the effect of the electrical conduction system according to an embodiment of the present invention. The method of FIG. 2 transforms medical image data of a patient to simulate cardiac EP of the patient over a period of time. It is to be understood that although the method of FIG. 2 models the electrical conduction system of the heart and simulates patient-specific cardiac electrophysiology for a patient, the method can be similarly applied to model any physical property of cardiac tissue based on a distance of the cardiac tissue from one or more anatomical structures and simulate cardiac function using the modeled physical properties of the cardiac tissue.

Referring to FIG. 2, at step 202, medical image data of the patient is received. The medical image data can be acquired using any type of medical imaging modality, such as computed tomography (CT), three-dimensional rotational angiography, magnetic resonance imaging (MRI), ultrasound (US), etc., provided that the heart is entirely visible in the medical image data. In an advantageous implementation, the medical image data includes three dimensional (3D) medical image data. The medical image data can be received directly from an image acquisition device, such as a CT scanner, a C-arm image-acquisition device, an MRI scanner, or an US scanner, or the medical image data can be received by loading previously stored cardiac image data of the patient. The medical image data may be pre-operative medical image data acquired prior to a cardiac EP intervention or intra-operative medical image data acquired during a cardiac EP intervention.

At step 204, a patient-specific anatomical heart model is generated from the medical image data of the patient. In order to generate the patient-specific anatomical heart model, a patient-specific heart morphology model is extracted from the medical image data. The patient-specific heart morphology model can be a comprehensive geometrical model that represents the patient-specific heart morphology. In an advantageous embodiment, the patient-specific heart morphology model includes individual anatomical models representing the morphology of various heart components. The models are highly modular and can be customized depending on the application. The complete heart model can comprise the left ventricle (LV), left atrium (LA), left outflow tract, aortic root, pulmonary veins, right ventricle (RV), right atrium (RA), right outflow tract, RV neck, and veins. Papillaries and trabeculae can also be obtained, from CT images for instance. Each of these components can be used individually or jointly according to data availability and clinical application. In an exemplary embodiment, the LV and RV anatomical models estimated from the pre-operative cardiac image data are used. In a possible implementation, only the LV and RV are explicitly modeled. In another possible implementation, models for all of the heart chambers are extracted. It is also possible that the comprehensive model including all of the heart components is extracted. The modularity of this framework enables using images in which only part of the anatomy is visible. For example, pre-operative US images can be used to extract the LV model, but the present invention is not limited thereto.

The anatomical model for each heart component can be extracted individually. In particular, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

Once the individual anatomical models for the various heart components are extracted from the medical image data patient-specific heart morphology model is fused into a single volumetric mesh representation and surface elements of the mesh are tagged into surface zones. For example, in the case of ventricular tachycardia (VT/VF) ablation therapy, the patient-specific LV and RV anatomical models can be fused into a single anatomical model of the bi-ventricular myocardium. In particular, the LV and RV anatomies that are extracted from the medical image data are fused into a single volumetric mesh representation. The LV and RV models can be fused into a single volumetric mesh representation, on which vertices are tagged into surface zones (LV endocardium, LV septum, RV endocardium, RV septum) according to the underlying anatomy of the estimated surface models. The tagging of the vertices of the mesh can provide automatic identification of geometrical landmarks on the patient-specific heart model. In particular, the septal portion of the right and left endocardium can be automatically identified and tagged on the patient-specific anatomical heart model. According to an advantageous embodiment, tetrahedral elements can be used to accurately represent the details of the bi-ventricular anatomy.

Certain types of medical imaging modalities, such as DE-MRI or CT perfusion, can be used to accurately localize scar tissue in a patient's heart. However, these types of medical image data may not be available for all patients. For example, because VT patients typically wear implantable cardioverter-defibrillator (ICD) devices already, a pre-operative MRI often cannot be performed to quantify the extent of the scar tissue. Even in the case of MRI-compatible ICD devices, the artifacts generated by the ICD electrodes in MRI images can compromise identification of the scar tissue. If scar imaging data is available for the patient, the scar tissue and grey zone tissue can be segmented in the medical imaging data and included in the patient-specific anatomical heart model. The grey zone tissue is a border zone surrounding the scar tissue that represents healing tissue. In an advantageous implementation, the scar tissue and border zone surrounding the scar tissue can be segmented by detecting myocardial borders of the heart in a sequence of image data (e.g., cine DE-MRI data) taken over multiple cardiac phases, and then classifying the detected myocardial borders as viable tissue or non-viable tissue (i.e., scar tissue) using a trained support vector machine (SVM), or other supervised learning technique. Such a method for segmenting scar tissue in DE-MRI image data is described in greater detail in U.S. Pat. No. 7,668,354, which is incorporated herein by reference. The segmented scar tissue and surrounding border zone is then mapped to the volumetric mesh representation of the heart chambers. For example, the tetrahedra shape of the volumetric mesh representation of the fused LV and LA can be locally modified to match the boundaries of the segmented scar tissue and border zone.

Certain types of imaging modalities, such as DynaCT, CT angiography, and MR, can provide imaging of the coronary arteries and veins. If such coronary sinus imaging data is available, centerlines of the coronary sinus can be automatically extracted from the medical image data and included in the patient-specific anatomical heart model. The method for coronary artery centerline extraction described in United States Published Patent Application No. 2013/0216110, which is incorporated herein by reference, can be used to extract the centerlines of the coronary sinus. The coronary sinus is then mapped to the volumetric mesh representation of the heart chambers. In an advantageous implementation, tetrahedra in the anatomical model belonging to the coronary sinus are tagged based on their distance from the extracted centerlines of the coronary sinus.

At step 206, a computational grid is generated from the patient-specific anatomical heart model. In an advantageous embodiment, a Cartesian grid domain for electrophysiology computations is generated from the patient-specific anatomical heart model. A Cartesian grid, possibly with unequal and spatially varying spacing, is first generated in a bounding box surrounding the anatomical model. Grid spacing can be defined by the user or fixed in the system. A coarse grid spacing can be used to increase simulation speed in order to provide real-time or near real-time cardiac EP simulation. A level-set representation is then calculated from the patient-specific anatomical mesh as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as septal nodes. Available scars and border zones are also reported in the domain through additional level-set information.

At step 208, the electrical conduction system of the heart of the patient is modeled on the computational grid by determining electrical properties of the cardiac tissue for each node of the computational grid. According to an advantageous embodiment, under the assumption that the left and right bundle branches, as well as the Purkinje fibers, are densely diffused in the subendocardium, the effect of the high-speed bundles can be modeled as a localized increase in the electrical diffusivity of the myocardial tissue in the endocardium. In order to achieve real-time cardiac EP simulation, embodiments of the present invention utilize the LBM-EP framework, which is based on a Cartesian computational grid. To model the fast-propagation tissue, the endocardial surface is rasterized on the computational grid, as described above in step 206, and grid cells corresponding to the fast-propagation tissue (e.g. Purkinje fibers) can be assigned a high diffusion coefficient $D_{Purkin}$. A limitation to this approach is that the thickness of the layer of high-speed conducting tissue cannot be controlled, i.e., it is always in the order of one grid cell. Accordingly, the thickness of the modeled high-speed conducting tissue changes if the spatial resolution of the grid changes. According to an advantageous embodiment, to overcome this limitation and obtain a grid-independent representation of the electrical conduction system of the heart, a rule is defined to classify the myocardial tissue as part of the high-speed bundles based on the distance of the myocardial tissue from the endocardium, with sub-grid accuracy. As a preliminary step, geometrical landmarks of the patient-specific heart model are automatically identified. In particular, the right and left endocardium are automatically located in the patient-specific anatomical heart model. A level-set approach is used to accurately calculate the distance field from the endocardium. If the distance of the myocardial tissue from the endocardium is smaller than a threshold value, the tissue is classified as high-speed conducting tissue. The diffusion coefficient assigned to each grid cell is a function of its volume fraction of high-speed conduction tissue.

Figure 3:
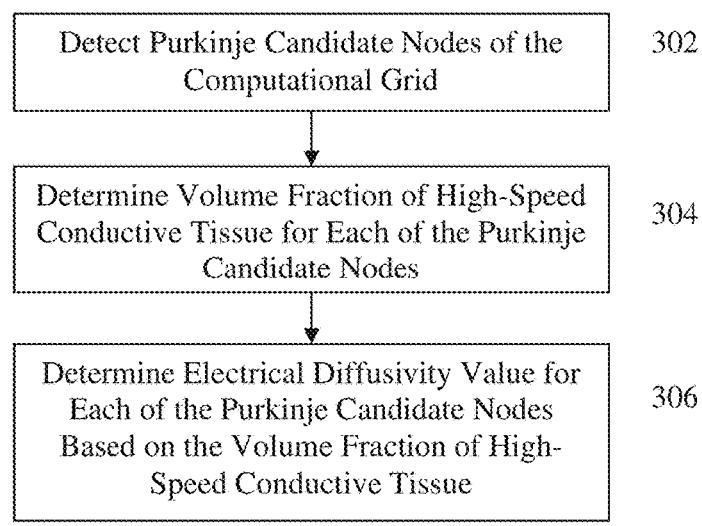
FIG. 3 illustrates a method of modeling the effect of the Purkinje network of a patient according to an embodiment of the present invention.

FIG. 3 illustrates a method of modeling the effect of the electrical conduction system of the heart of a patient according to an embodiment of the present invention. The method of FIG. 3 can be used to implement step 208 of FIG. 2. The method of FIG. 3 determines an electrical diffusivity value for each node of the patient-specific anatomical model in the computational grid. The electrical diffusivity D is defined as a piecewise constant field over the Cartesian grid, modeling each grid point as the center of a voxel or a volume of tissue. The diffusivity value assigned to each grid point ranges from normal to high based on the volume fraction p of tissue within the voxel whose distance from the endocardium is smaller than a threshold T. For every lattice node x, the electrical diffusivity K can be determined as:

$$D(x) = D_{Purkin}\psi + D_{normal}(1-\psi) \quad (1)$$

where $K_{Purkin}$ is an electrical diffusivity value for high-speed conducting tissue, $K_{normal}$ is an electrical diffusivity value for normal tissue, and $\psi$ is the volume fraction of high speed tissue within the voxel centered at the node x.

Referring to FIG. 3, at step 302, candidate Purkinje nodes of the computational grid are detected based on a distance from the endocardium. The candidate Purkinje nodes are grid points of the computational grid that may have a partial volume of high-speed conducting tissue. The candidate Purkinje nodes are detected by selecting all nodes whose distance from the endocardium is less than an extended threshold $\tau_{ext}$, corresponding to the thickness of the layer of high-speed conducting tissue plus the maximum distance between the barycenter of the voxel and its boundary:

$$\tau_{ext} = \tau + \frac{\sqrt{3}}{2}h \quad (2)$$

where $\tau$ is a threshold representing the thickness of the layer of high-speed conducting tissue and h denotes the spacing of the lattice (computational grid). A distance field from the endocardium is calculated using a level set approach and the Purkinje candidate nodes are selected based on the distance field. That is, if $\phi$ denotes a level-set representation of the endocardial surface, its discretization $\phi_h$ over the Cartesian grid is calculated, and the Purkinje candidate nodes are detected by selecting all lattice nodes x such that $\phi_h(\hat{x}) < \tau_{ext}$.

At step 304, a volume fraction of high speed conductive tissue is determined for each of the Purkinje candidate nodes. For each candidate voxel centered at a Purkinje candidate node $\hat{x}$, a sub-grid of nodes $\hat{\xi} \in \hat{v}$ is defined with uniform spacing $\hat{h} < h$. For example, $\hat{h}$ can selected to be one tenth of h, but the present invention is not limited thereto. In exemplary implementation, h can be mm and $\hat{h}$ can be 0.1 mm. A distance field from the endocardium is created at a sub-grid resolution by calculating the discretization of the level set function of the endocardium on the sub-grid $\hat{\phi}_{\hat{h}} = \phi|_{\hat{v}}$. The nodes of the sub-grid are then classified as normal or high-speed conducting tissue based on their distance from the endocardium using the discretization of the level set function of the endocardium on the sub-grid:

$$\forall \xi \in \hat{v}: \begin{cases} \hat{\phi}_h(\xi) \leq \tau \rightarrow \text{High-speed conducting tissue} \\ \hat{\phi}_h(\xi) > \tau \rightarrow \text{Normal tissue} \end{cases} \quad (3)$$

where τ is the threshold that represents the thickness of the high-speed conducting layer. The threshold τ can be set by a user or can be determined using a histological standard reference value. In an exemplary implementation, a threshold of τ=1 mm can be used, but the present invention is not limited thereto. It is also possible that the threshold τ varies spatially to represent different thicknesses of the electrical conduction system at different locations in the endocardium. Once the nodes of the sub-grid are classified as high-speed conducting tissue or normal tissue for a Purkinje candidate node, the volume fraction ψ is calculated for that Purkinje candidate node as the number of sub-grid nodes belonging to the high-speed conducting tissue over the total number of sub-grid nodes.

At step 306, the electrical diffusivity value for each of the Purkinje candidate nodes is calculated based on the volume fraction p calculated for each of the Purkinje candidate nodes. In an exemplary implementation, the electrical diffusivity value for each node on the myocardium in the computational grid is calculated as $D(x)=D_{Purkin}\psi+D_{normal}(1-\psi)$. For each of the Purkinje candidate nodes, the volume fraction ψ of the high-speed conductive tissue calculated in step 304 is used to calculate the electrical diffusivity value. For other nodes on the myocardium that were not selected as Purkinje candidate nodes, it is assumed that the volume fraction ψ of high-speed conductive tissue is equal to zero, and the electrical diffusivity value $D_{normal}$ for normal tissue is assigned to those nodes. The electrical diffusivity value $D_{normal}$ for normal tissue can be set using literature values or can be the result of the personalization of the EP model. The electrical diffusivity value $D_{Purkin}$ for high-speed conductive tissue is higher than $D_{normal}$. In an exemplary implementation, the electrical diffusivity value for the high-speed conductive tissue $D_{Purkin}$ can be set to be 16 times the normal value $D_{normal}$, representing a layer of fiber that has a maximum conduction velocity that is approximately four times larger than that of normal tissue For example, $D_{Purkin}$ in the order of 2000 mm²/s and $D_{normal}$ can be in the order of 100 mm²/s. In another exemplary implementation, $D_{normal}$ and $D_{Purkin}$ are found as the result of the personalization of the EP model.

Figure 4:
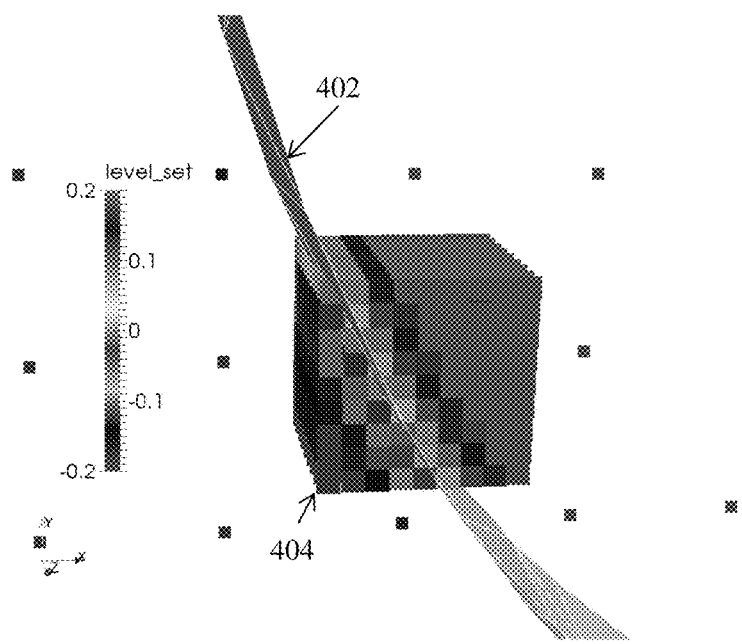
FIG. 4 illustrates a graphical representation of the modeling approach for high-speed conducting tissue according to an embodiment of the present invention.

FIG. 4 illustrates a graphical representation of the modeling approach for high-speed conducting tissue according to an embodiment of the present invention. FIG. 4 shows how the method of FIG. 3 provides an accurate evaluation of the volume fraction of tissue within a given distance from the endocardium surface. As illustrated in FIG. 4, the lattice nodes of the Cartesian grid are shown in the background as squares. The triangulated surface 402 represents the endocardium. For one of the lattice nodes, the sub-grid 404 defined in the voxel centered at that lattice node is visualized, each point in the sub-grid 404 being colored by the value of the level set (shown here in black and white), representing the distance of each point in the sub-grid 404 from the endocardium surface 402. In this example, a threshold of τ=0.1 mm is utilized. For visualization purposes, the color bar (shown here in black and white) has been scaled to the interval [−0.2; 0.2] mm.

The method of FIG. 3 classifies tissue as normal or high-speed conducting based on the evaluation of a distance function from the endocardium. In the model described herein, we assume that electrical diffusivity is a linear function of the distance from the endocardium, however the invention is not limited thereto. If this distance function is represented as a discretized field over the Cartesian grid (in particular, we approximate this function over the Cartesian grid by piecewise constant interpolation), the grid size limits the accuracy in the identification of the high-speed conducting tissue. To avoid inaccuracies, the method of FIG. 3 performs local evaluation of the distance function with higher spatial resolution, through the definition of "nested" level set representations of the endocardial surface. That is, the method of FIG. 3 uses a first level set representation of the endocardium discretized on the coarse resolution of the computational grid to determine which grid nodes may include high-speed conducting tissue and then uses a second level set representation discretized at a higher spatial resolution only on sub-grids defined within voxels corresponding to the detected candidate grid nodes to determine the volume fraction of high-speed conducting tissue for the candidate grid nodes. This allows the discretization of the distance function with an accuracy that is not limited by the size of the lattice. For this reason, the method of FIG. 3 is effective especially when the spacing of the original lattice is of the same order of magnitude of the threshold τ, or larger. If the electrical diffusivity in the voxel shown in FIG. 4 would have been assigned based on its distance from the surface (as evaluated on the original lattice), the entire volume of tissue would have been classified as high-speed conducting, resulting in a less accurate determination of the electrical diffusivity value for that voxel.

Returning to FIG. 2, at step 210, patient-specific cardiac EP simulation is performed using the patient-specific electrical diffusivity values determined in step 208. In particular, cardiac electrophysiology is calculated at each node of the Cartesian grid domain within the myocardium at each of a plurality of time steps. In a possible implementation, the patient-specific cardiac EP simulation may be performed in real-time during an intervention procedure to guide the intervention procedure. It is also possible that the patient-specific cardiac EP simulation can be performed for intervention planning prior to an intervention. According to an advantageous embodiment, the cardiac electrophysiology is calculated at each node within the myocardium using the Lattice-Boltzmann Method for Electrophysiology (LBM-EP) to solve a cardiac electrophysiology model at each node. The cardiac electrophysiology model calculates the variation of the transmembrane potential v(x,t) over time according to the mono-domain equation:

$$\frac{dv(x,t)}{dt} = R(x,t) + \nabla \cdot D(x)K(x)\nabla v(x,t), \quad (4)$$

where R(x,t) is a reaction term describing the cellular mechanisms giving rise to the action potential, and D(x) is the local diffusivity defined in equation (1). The values $D_{Purkin}$ and $D_{normal}$ can be estimated from the patient-specific data, and D(x) can be computed for each node as in step 208. Finally, K(x) is the anisotropy matrix defined by $(1-\rho)f(x)f(x)^T+\mu Id$, ρ being the ratio between the cross-fiber diffusivity and the fiber diffusivity (typically ρ=0.11-0.25). It is also possible to use orthotropic or fully anisotropic tensors K(x) for improved characterization of the fiber architecture.

The choice of the reaction term R(x,t) depends on the cellular model of cardiac electrophysiology that is used. The method disclosed herein is modular in that it can handle any standard mono-domain models, such as, but not limited to the "Mitchell-Schaffer model" proposed in Mitchell et al., "A Two-Current Model for the Dynamics of Cardiac Membrane", *Bulletin of Mathematical Biology*, 65(5):767-793, 2003, or the model proposed in Ten Tusscher, et al., "Cell Model for Efficient Simulation of Wave Propagation in Human Ventricular Tissue Under Normal and Pathological Conditions", *Physics in Medicine and Biology*, 51, pp 6141, 2006. For the Mitchell-Schaeffer model for instance, we have:

$$R(x, t) = \frac{h(x, t)v^2(x, t)(1 - v(x, t))}{\tau_{in}} - \frac{v(x, t)}{\tau_{out}} + J_{stim}(X). \quad (5)$$

In this equation $J_{stim}(x)$ is an external stimulus current. In intraoperative intervention planning, when the electrophysiologist is pacing the heart at a given location, the position of the pacing catheter is tracked using an embedded tracking method (e.g., electromagnetic tracking, bi-plane image-based tracking, etc.), and the position of the pacing catheter returned by the embedded tracking method is used to add a stimulus current to the model through $J_{stim}(x)$ at the acquired position. Virtual pacing is achieved by adding $J_{stim}(x)$ at a spatial location chosen by the user or chosen automatically by the system. The amount of current that is added to the model is obtained from the catheter manufacturer specifications.

In Equation (5), h(x,t) is a gating variable that controls the state of the ion channels according to the following ordinary differential equation:

$$\frac{dh(x, t)}{dt} = \begin{cases} \frac{1 - h(x, t)}{\tau_{open}} & \text{if } v(x, t) < v_{gate} \\ \frac{-h(x, t)}{\tau_{close}} & \text{otherwise} \end{cases}$$

$v_{gate}$ is a potential threshold, and $\tau_{in}$, $\tau_{out}$, $\tau_{open}$ and $\tau_{close}$ are parameters controlling the shape of the action potential. The maximum action potential duration APD(x) is directly related to $\tau_{close}(x)$ according to the formula $APD_{max}(x) = \tau_{close}(x)\ln(\tau_{out}/(4\tau_{in}))$. In an exemplary embodiment, patient-specific values for D(x) and $\tau_{close}(x)$ can be estimated, the other parameters are kept constant to their default (i.e. nominal) values. However, it is also possible to determine patient-specific values for additional parameters as well. The patient-specific values for D(x) and $APD_{max}(x)/\tau_{close}(x)$ can be estimated by iterative optimization of these parameters based on a comparison of simulated EP and observed patient data, such as ECG measurements of the patient, invasive electrophysiology mapping of the patient, or a body surface potential mapping of the patient. For example, the patient-specific EP model parameters can be estimated using the method described in U.S. Published Patent Application No. 2015/0042646, entitled "System and Method for Patient Specific Planning and Guidance of Electrophysiology Interventions," which is incorporated herein by reference in its entirety.

Equation (4) is solved using LBM-EP, which is a highly parallelizable algorithm to solve mono-domain electrophysiology equations. The LBM-EP algorithm is described in greater detail in United States Published Patent Application No. 2013/0226542, entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. Since the method is node-wise, the algorithm is highly parallelizable. In an advantageous embodiment, the method can be implemented on a graphics processing unit (GPU), which enables near real-time and accurate cardiac electrophysiology computation during an intervention.

In addition to the cardiac EP, torso potentials and ECG signals can be simulated based on the patient-specific cardiac EP model. The patient-specific cardiac EP model calculates the transmembrane potential v(x,t) at each node within the myocardium. Once the transmembrane potential v(x,t) is calculated, the extra-cellular potential $\phi_e$ at each node can be calculated using a closed-form expression ($\Omega$ defines the computational domain; $|\Omega|$ is the number of elements therein):

$$\phi_e(x, t) = \frac{\lambda}{1 + \lambda} \frac{1}{|\Omega|} \int_\Omega [v(y, t) - v(x, t)] dy$$

where $\lambda$ is a constant diffusion anisotropy ratio, $\lambda = D_i(x)/D_e(x)$, and $D_i$ and $D_e$ are intra- and extra-cellular diffusivity tensors. The extra-cellular potential $\phi_e$ is then mapped back to the epicardium surface mesh using tri-linear interpolation. Furthermore, the extra-cellular potentials are projected onto the torso surface using a boundary element method (BEM). The potential $\phi(x)$ at any point x of the thoracic domain can be calculated as:

$$\phi(x) = \frac{1}{4\pi} \int_{S_B} \phi_b \frac{r \cdot n}{\|r\|^3} dS_B - \frac{1}{4\pi} \int_{S_H} \left[ \phi_e \frac{r \cdot n}{\|r\|^3} + \frac{\nabla \phi_e \cdot n}{\|r\|} \right] dS_H$$

where r is the vector defined by x and the integration point, while $S_B$ and $S_H$ are the torso and epicardium surfaces, respectively. The body surface potential at the torso, $\phi_b$, can be expressed as a function of the extra-cellular potential $\phi_e$, which allows the potential to be calculated at any point on the torso. According to an advantageous implementation, a torso mesh can be segmented from the medical image data using machine learning algorithms and the body surface potential $\phi_b$ can be calculated for each vertex on the torso mesh. ECG signals can be calculated based on the torso potentials. Based on the body surface potentials, which are computed for each vertex at the torso mesh, the potential at all of the standard ECG lead locations is estimated, resulting in simulated ECG signals.

At step 212, results of the patient-specific cardiac EP simulation are output. For example, visualizations of the simulated cardiac electrophysiology at each node in the Cartesian grid domain within the myocardium can be output, including a time varying 3D action potential map; a 3D map of depolarization times $t_{dep}(x)|v(x,t_{dep}-dt)<v_{gate}$, $v(x,t_{dep})>v_{gate}$; and a 3D map of repolarization times $t_{rep}(x)|v(x,t_{dep}-dt)>v_{gate}$, $v(x,t_{dep})<V_{gate}$. Additionally, other guidance maps, such as a 3D map of tissue diffusivity D(x) (resulting from step 208), a 3D map of action potential duration APD(x) can also be output. In addition, time varying maps of body surface potentials and simulated ECG signals can also be output. The simulation results can be output by displaying the results, for example on a display screen of a computer system. In a possible implementation, these results can be displayed in real-time during an intervention procedure to guide the physician performing the intervention procedure. In order to provide patient-specific planning and/or guidance of an intervention procedure, various virtual pacing catheter locations can be received, either by user input or by automatic systematic virtual pacing, and various EP simulations corresponding to the virtual pacing catheter locations can be performed.

As described above, the method of FIG. 3 determines electrical diffusivity for each of the grid points of the computational grid, however the present invention is not limited thereto, and can be similarly applied to other EP model parameters in addition to electrical diffusivity that have a spatial dependence requiring sub-grid accuracy. Although the method described above assumes that electrical diffusivity is a linear function of the distance from the endocardium, the present invention is not limited to linear relationships, and can be similarly applied to cases in which model parameters depend non-linearly on a spatial position. The methods described above are applied to modeling the effect of the Purkinje network. Such methods can be similarly applied to model the effect of other physical phenomena, such as scar tissue and border zones, as well. Moreover, the same methods can be applied to other physical parameters of the cardiac tissue in addition to EP parameters, including but not limited to tissue density, tissue stiffness, tissue histology.

Figure 5:
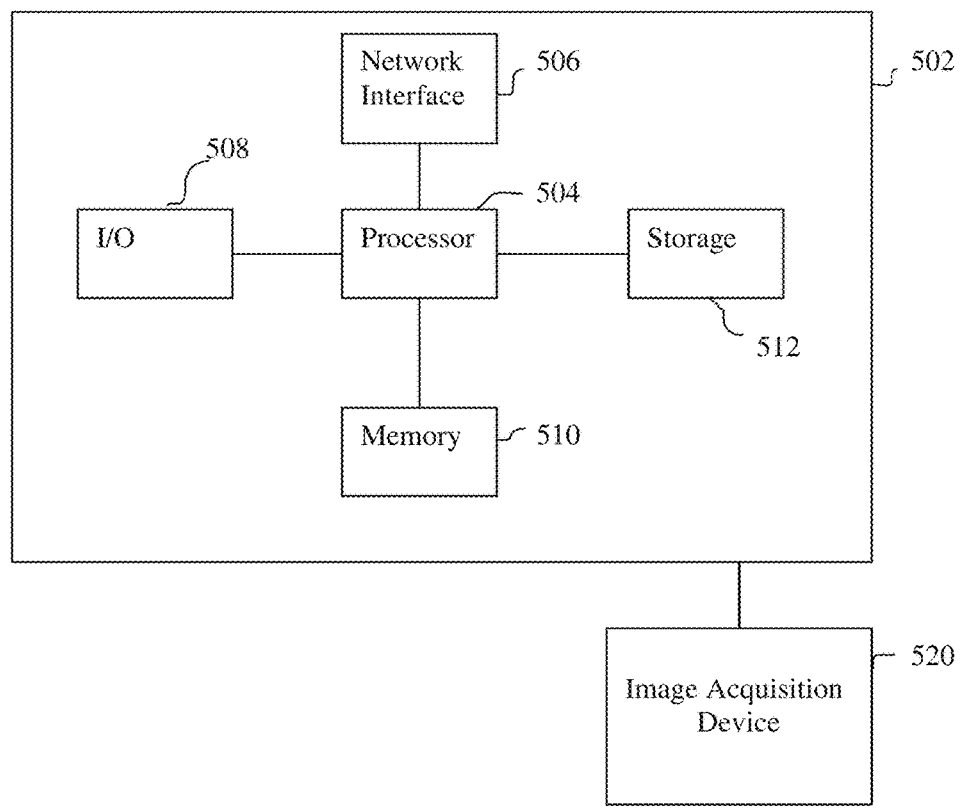
FIG. 5 is a high-level block diagram of a computer capable of implementing the present invention.

The above-described methods for simulation of patient-specific cardiac EP including the effect of the Purkinje system can be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk or a non-transitory computer readable medium) and loaded into memory 510 when execution of the computer program instructions is desired. Thus, the steps of the methods of FIGS. 2 and 3 may be defined by the computer program instructions stored in the memory 510 and/or storage 512 and controlled by the processor 504 executing the computer program instructions. An image acquisition device 520, such as a CT scanning device, C-arm image acquisition device, MR scanning device, Ultrasound device, etc., can be connected to the computer 502 to input image data to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for patient-specific simulation of cardiac function, comprising:
    generating a patient-specific anatomical heart model from cardiac image data of a patient;
    modeling physical properties of cardiac tissue in the patient-specific anatomical heart model based on a distance of the cardiac tissue from one or more anatomical structures in the patient-specific anatomical heart model; and
    simulating cardiac function for the patient using a cardiac model with the physical properties modeling based on the distance of the cardiac tissue from the one or more anatomical structures in the patient-specific anatomical heart model; and
    wherein the modeling physical properties of cardiac tissue in the patient-specific anatomical heart model based on a distance of the cardiac tissue from one or more anatomical structures in the patient-specific anatomical heart model and the simulating cardiac function for the patient using a cardiac model with the physical properties modeling based on the distance of the cardiac tissue from the one or more anatomical structures in the patient-specific anatomical heart model are performed in real-time during a cardiac intervention procedure.

2. The method of claim 1, wherein modeling physical properties of cardiac tissue in the patient-specific anatomical heart model based on a distance of the cardiac tissue from one or more anatomical structures in the patient-specific anatomical heart model comprises:
    modeling an electrical conduction system of the heart of the patient by determining electrical properties of cardiac tissue in the patient-specific anatomical heart model based on a distance of the cardiac tissue from an anatomical structure in the patient-specific anatomical heart model.

3. The method of claim 2, wherein simulating cardiac function for the patient using a cardiac model with the physical properties modeling based on the distance of the cardiac tissue from the one or more anatomical structures in the patient-specific anatomical heart model comprises:
    simulating cardiac electrophysiology for the patient using a cardiac electrophysiology model with the electrical properties determined to model the electrical conduction system of the heart of the patient.

4. The method of claim 3, wherein modeling an electrical conduction system of the heart of the patient by determining electrical properties of cardiac tissue in the patient-specific anatomical heart model based on a distance of the cardiac tissue from an anatomical structure in the patient-specific anatomical heart model comprises:

modeling the electrical conduction system of the heart of the patient by determining electrical diffusivity values of cardiac tissue in the patient-specific anatomical heart model based on a distance of the cardiac tissue from an epicardium in the patient-specific anatomical heart model.

5. The method of claim 4, wherein simulating cardiac electrophysiology for the patient using a cardiac electrophysiology model with the electrical properties determined to model the electrical conduction system of the heart of the patient comprises:

simulating cardiac electrophysiology for the patient using the cardiac electrophysiology model with the electrical diffusivity values determined to model the electrical conduction system of the heart of the patient.

6. The method of claim 3, wherein modeling an electrical conduction system of the heart of the patient by determining electrical properties of cardiac tissue in the patient-specific anatomical heart model based on a distance of the cardiac tissue from an anatomical structure in the patient-specific anatomical heart model comprises:

calculating a distance field from the endocardium on a computational grid corresponding to the patient-specific anatomical heart model with sub-grid accuracy using a nested level-set discretization of the endocardial surface; and calculating an electrical diffusivity value at each of a plurality of points on the computation grid as a function of the distance of cardiac tissue within a voxel corresponding to each of the plurality of points from the endocardium surface.

7. The method of claim 5, further comprising:
generating a computational grid from the patient-specific anatomical heart model.

8. The method of claim 7, wherein modeling the electrical conduction system of the heart of the patient by determining electrical diffusivity values of cardiac tissue in the patient-specific anatomical heart model based on a distance of the cardiac tissue from an epicardium in the patient-specific anatomical heart model comprises:

detecting, from a plurality of nodes of the computational grid, a set of Purkinje candidate nodes based on a distance of each node from the septal endocardium;

calculating, for each of the Purkinje candidate nodes, a volume fraction of high-speed conductive tissue within a voxel corresponding to the Purkinje candidate node; and calculating the electrical diffusivity value for each of the Purkinje candidate nodes as a function of the volume fraction of high-speed conductive tissue calculated for the Purkinje candidate node.

9. The method of claim 8, wherein detecting, from a plurality of nodes of the computational grid, a set of Purkinje candidate nodes based on a distance of each node from the septal endocardium comprises:

calculating a first distance field from the septal endocardium by calculating a discretization of a level-set representation of the endocardial surface over the computational grid; and for each of the plurality of nodes on the computational grid, selecting the node as a Purkinje candidate node if a value of the first distance field at the node is less than a first threshold.

10. The method of claim 9, wherein calculating, for each of the Purkinje candidate nodes, a volume fraction of high-speed conductive tissue within a voxel corresponding to the Purkinje candidate node comprises, for each of the Purkinje candidate nodes:

defining a sub-grid of nodes within the voxel corresponding to the Purkinje candidate node;

calculating a second distance field from the septal endocardium by calculating a discretization of the level-set representation of the endocardial surface over the sub-grid defined for the Purkinje candidate node;

for each of the nodes in the sub-grid of nodes within the voxel corresponding to the Purkinje candidate node, classifying the node as high-speed conductive tissue if a value of the second distance field at the node is less than a second threshold and classifying the node as normal tissue if a value of the second distance field at the node is greater than the second threshold; and calculating the volume fraction of high-speed conductive tissue within the voxel corresponding to the Purkinje candidate node as a number of nodes in the sub-grid of nodes classified as high-speed conductive tissue over a total number of nodes in the sub-grid of nodes.

11. The method of claim 8, wherein calculating the electrical diffusivity value for each of the Purkinje candidate nodes as a function of the volume fraction of high-speed conductive tissue calculated for the Purkinje candidate node comprises:

calculating the electrical diffusivity value for each of the Purkinje candidate nodes as $D(x)=D_{Purkin}\psi+D_{normal}(1-\psi)$, where $D_{Purkin}$ is an electrical diffusivity value for high-speed conductive tissue, $D_{normal}$ is an electrical diffusivity value for normal tissue, and is the volume fraction of high-speed conductive tissue within the voxel centered at the node x.

12. The method of claim 11, wherein modeling a Purkinje network of the patient by determining electrical diffusivity values of cardiac tissue in the patient-specific anatomical heart model based on a distance of the cardiac tissue from a septal endocardium in the patient-specific anatomical heart model further comprises:

determining the electrical diffusivity value for each of the plurality of nodes of the computational grid not detected to be Purkinje candidate nodes to be $D_{normal}$.

13. The method of claim 1, wherein generating a patient-specific anatomical heart model from cardiac image data of a patient comprises:

extracting a multi-component patient-specific heart morphology model from the cardiac image data; and fusing the multi-component patient-specific heart morphology model into a single heart model and tagging elements of the single heart model according to the multiple components.

14. The method of claim 13, wherein tagging elements of the single heart model according to the multiple components comprises:

automatically identifying and tagging an endocardium in the single heart model.

15. The method of claim 5, wherein simulating cardiac electrophysiology for the patient using the cardiac electrophysiology model with the electrical diffusivity values determined to model the electrical conduction system of the heart of the patient comprises:

calculating transmembrane potential variation over time at each of a plurality of nodes within the myocardium in a computational grid corresponding to the patient-specific anatomical heart model by computing a solution of the cardiac electrophysiology model using the electrical diffusivity values determined to model the Purkinje network of the patient for each of the plurality of nodes using a Lattice-Boltzmann method for electrophysiology.

16. The method of claim 3, wherein the modeling an electrical conduction system of the heart of the patient by determining electrical properties of cardiac tissue in the patient-specific anatomical heart model based on a distance of the cardiac tissue from an anatomical structure in the patient-specific anatomical heart model and the simulating cardiac electrophysiology for the patient using a cardiac electrophysiology model with the electrical properties determined to model the electrical conduction system of the heart of the patient are performed in real-time during a cardiac electrophysiology intervention procedure.

17. An apparatus for patient-specific simulation of cardiac function, comprising:
a processor:
a memory coupled with the processor, the memory having a program that stores computer program instructions that when executed cause the processor to perform operations for:
generating a patient-specific anatomical heart model from cardiac image data of a patient;
modeling physical properties of cardiac tissue in the patient-specific anatomical heart model based on a distance of the cardiac tissue from one or more anatomical structures in the patient-specific anatomical heart model; and
simulating cardiac function for the patient using a cardiac model with the physical properties modeling based on the distance of the cardiac tissue from the one or more anatomical structures in the patient-specific anatomical heart model; and
wherein the modeling physical properties of cardiac tissue in the patient-specific anatomical heart model based on a distance of the cardiac tissue from one or more anatomical structures in the patient-specific anatomical heart model and the simulating cardiac function for the patient using a cardiac model with the physical properties modeling based on the distance of the cardiac tissue from the one or more anatomical structures in the patient-specific anatomical heart model are performed in real-time during a cardiac intervention procedure.

18. The apparatus of claim 17, wherein the modeling physical properties of cardiac tissue in the patient-specific anatomical heart model based on a distance of the cardiac tissue from one or more anatomical structures in the patient-specific anatomical heart model comprises:
modeling an electrical conduction system of the heart of the patient by determining electrical properties of cardiac tissue in the patient-specific anatomical heart model based on a distance of the cardiac tissue from an anatomical structure in the patient-specific anatomical heart model.

19. The apparatus of claim 18, wherein the simulating cardiac function for the patient using a cardiac model with the physical properties modeling based on the distance of the cardiac tissue from the one or more anatomical structures in the patient-specific anatomical heart model further comprises:
simulating cardiac electrophysiology for the patient using a cardiac electrophysiology model with the electrical properties determined to model the electrical conduction system of the heart of the patient.

20. The apparatus of claim 19, wherein the modeling an electrical conduction system of the heart of the patient by determining electrical properties of cardiac tissue in the patient-specific anatomical heart model based on a distance of the cardiac tissue from an anatomical structure in the patient-specific anatomical heart model further comprises:
modeling the electrical conduction system of the heart of the patient by determining electrical diffusivity values of cardiac tissue in the patient-specific anatomical heart model based on a distance of the cardiac tissue from an epicardium in the patient-specific anatomical heart model.

21. The apparatus of claim 20, wherein the simulating cardiac electrophysiology for the patient using a cardiac electrophysiology model with the electrical properties determined to model the electrical conduction system of the heart of the patient further comprises:
simulating cardiac electrophysiology for the patient using the cardiac electrophysiology model with the electrical diffusivity values determined to model the electrical conduction system of the heart of the patient.

22. The apparatus of claim 19, wherein the modeling an electrical conduction system of the heart of the patient by determining electrical properties of cardiac tissue in the patient-specific anatomical heart model based on a distance of the cardiac tissue from an anatomical structure in the patient-specific anatomical heart model further comprises:
calculating a distance field from the endocardium on a computational grid corresponding to the patient-specific anatomical heart model with sub-grid accuracy using a nested level-set discretization of the endocardial surface; and
calculating an electrical diffusivity value at each of a plurality of points on the computation grid as a function of the distance of cardiac tissue within a voxel corresponding to each of the plurality of points from the endocardium surface.

23. The apparatus of claim 21, wherein the operations further comprise:
generating a computational grid from the patient-specific anatomical heart model.

24. The apparatus of claim 23, wherein the modeling the electrical conduction system of the heart of the patient by determining electrical diffusivity values of cardiac tissue in the patient-specific anatomical heart model based on a distance of the cardiac tissue from an epicardium in the patient-specific anatomical heart model further comprises:
detecting, from a plurality of nodes of the computational grid, a set of Purkinje candidate nodes based on a distance of each node from the septal endocardium;
calculating, for each of the Purkinje candidate nodes, a volume fraction of high-speed conductive tissue within a voxel corresponding to the Purkinje candidate node; and
calculating the electrical diffusivity value for each of the Purkinje candidate nodes as a function of the volume fraction of high-speed conductive tissue calculated for the Purkinje candidate node.

25. The apparatus of claim 24, wherein the detecting, from a plurality of nodes of the computational grid, a set of Purkinje candidate nodes based on a distance of each node from the septal endocardium further comprises:
calculating a first distance field from the septal endocardium by calculating a discretization of a level-set representation of the endocardial surface over the computational grid; and selecting, a node on the computational grid as a Purkinje candidate node if a value of the first distance field at the node is less than a first threshold.

26. The apparatus of claim 25, wherein the calculating, for each of the Purkinje candidate nodes, a volume fraction of high-speed conductive tissue within a voxel corresponding to the Purkinje candidate node further comprises:
   defining a sub-grid of nodes within the voxel corresponding to each Purkinje candidate node;
   calculating a second distance field from the septal endocardium by calculating a discretization of the level-set representation of the endocardial surface over the sub-grid defined for each Purkinje candidate node;
   classifying a node in the sub-grid of nodes within the voxel corresponding to each Purkinje candidate node as high-speed conductive tissue if a value of the second distance field at the node is less than a second threshold and classifying the node as normal tissue if a value of the second distance field at the node is greater than the second threshold; and
   calculating the volume fraction of high-speed conductive tissue within the voxel corresponding to each Purkinje candidate node as a number of nodes in the sub-grid of nodes classified as high-speed conductive tissue over a total number of nodes in the sub-grid of nodes.

27. The apparatus of claim 24, wherein the calculating the electrical diffusivity value for each of the Purkinje candidate nodes as a function of the volume fraction of high-speed conductive tissue calculated for the Purkinje candidate node further comprises:
   calculating the electrical diffusivity value for each of the Purkinje candidate nodes as $D(x)=D_{Purkin}\psi+D_{normal}(1-\psi)$, where $D_{Purkin}$ is an electrical diffusivity value for high-speed conductive tissue, $D_{normal}$ is an electrical diffusivity value for normal tissue, and $\psi$ is the volume fraction of high-speed conductive tissue within the voxel centered at the node x.

28. The apparatus of claim 27, wherein the modeling a Purkinje network of the patient by determining electrical diffusivity values of cardiac tissue in the patient-specific anatomical heart model based on a distance of the cardiac tissue from a septal endocardium in the patient-specific anatomical heart model further comprises:
   determining the electrical diffusivity value for each of the plurality of nodes of the computational grid not detected to be Purkinje candidate nodes to be $D_{normal}$.

29. The apparatus of claim 17, wherein the generating a patient-specific anatomical heart model from cardiac image data of a patient further comprises:
   extracting a multi-component patient-specific heart morphology model from the cardiac image data; and
   fusing the multi-component patient-specific heart morphology model into a single heart model and tagging elements of the single heart model according to the multiple components.

30. The apparatus of claim 29, wherein the fusing the multi-component patient-specific heart morphology model into a single heart model and tagging elements of the single heart model according to the multiple components further comprises:
   automatically identifying and tagging an endocardium in the single heart model.

31. The apparatus of claim 21, wherein the simulating cardiac electrophysiology for the patient using the cardiac electrophysiology model with the electrical diffusivity values determined to model the electrical conduction system of the heart of the patient further comprises:
   calculating transmembrane potential variation over time at each of a plurality of nodes within the myocardium in a computational grid corresponding to the patient-specific anatomical heart model by computing a solution of the cardiac electrophysiology model using the electrical diffusivity values determined to model the Purkinje network of the patient for each of the plurality of nodes using a Lattice-Boltzmann method for electrophysiology.

32. A non-transitory computer readable medium storing computer program instructions for patient-specific simulation of cardiac function, the computer program instructions when executed by a processor cause the processor to perform operations comprising:
   generating a patient-specific anatomical heart model from cardiac image data of a patient;
   modeling physical properties of cardiac tissue in the patient-specific anatomical heart model based on a distance of the cardiac tissue from one or more anatomical structures in the patient-specific anatomical heart model; and
   simulating cardiac function for the patient using a cardiac model with the physical properties modeling based on the distance of the cardiac tissue from the one or more anatomical structures in the patient-specific anatomical heart model; and
   wherein the modeling physical properties of cardiac tissue in the patient-specific anatomical heart model based on a distance of the cardiac tissue from one or more anatomical structures in the patient-specific anatomical heart model and the simulating cardiac function for the patient using a cardiac model with the physical properties modeling based on the distance of the cardiac tissue from the one or more anatomical structures in the patient-specific anatomical heart model are performed in real-time during a cardiac intervention procedure.

33. The non-transitory computer readable medium of claim 32, wherein modeling physical properties of cardiac tissue in the patient-specific anatomical heart model based on a distance of the cardiac tissue from one or more anatomical structures in the patient-specific anatomical heart model comprises:
   modeling an electrical conduction system of the heart of the patient by determining electrical properties of cardiac tissue in the patient-specific anatomical heart model based on a distance of the cardiac tissue from an anatomical structure in the patient-specific anatomical heart model.

34. The non-transitory computer readable medium of claim 33, wherein simulating cardiac function for the patient using a cardiac model with the physical properties modeling based on the distance of the cardiac tissue from the one or more anatomical structures in the patient-specific anatomical heart model comprises:
   simulating cardiac electrophysiology for the patient using a cardiac electrophysiology model with the electrical properties determined to model the electrical conduction system of the heart of the patient.

35. The non-transitory computer readable medium of claim 34, wherein modeling an electrical conduction system of the heart of the patient by determining electrical properties of cardiac tissue in the patient-specific anatomical heart model based on a distance of the cardiac tissue from an anatomical structure in the patient-specific anatomical heart model comprises:
   modeling the electrical conduction system of the heart of the patient by determining electrical diffusivity values of cardiac tissue in the patient-specific anatomical heart model based on a distance of the cardiac tissue from an epicardium in the patient-specific anatomical heart model.

36. The non-transitory computer readable medium of claim 35, wherein simulating cardiac electrophysiology for the patient using a cardiac electrophysiology model with the electrical properties determined to model the electrical conduction system of the heart of the patient comprises:
simulating cardiac electrophysiology for the patient using the cardiac electrophysiology model with the electrical diffusivity values determined to model the electrical conduction system of the heart of the patient.

37. The non-transitory computer readable medium of claim 34, wherein modeling an electrical conduction system of the heart of the patient by determining electrical properties of cardiac tissue in the patient-specific anatomical heart model based on a distance of the cardiac tissue from an anatomical structure in the patient-specific anatomical heart model comprises:
calculating a distance field from the endocardium on a computational grid corresponding to the patient-specific anatomical heart model with sub-grid accuracy using a nested level-set discretization of the endocardial surface; and
calculating an electrical diffusivity value at each of a plurality of points on the computation grid as a function of the distance of cardiac tissue within a voxel corresponding to each of the plurality of points from the endocardium surface.

38. The non-transitory computer readable medium of claim 36, wherein the operations further comprise:
generating a computational grid from the patient-specific anatomical heart model.

39. The non-transitory computer readable medium of claim 38, wherein modeling the electrical conduction system of the heart of the patient by determining electrical diffusivity values of cardiac tissue in the patient-specific anatomical heart model based on a distance of the cardiac tissue from an epicardium in the patient-specific anatomical heart model comprises:
detecting, from a plurality of nodes of the computational grid, a set of Purkinje candidate nodes based on a distance of each node from the septal endocardium;
calculating, for each of the Purkinje candidate nodes, a volume fraction of high-speed conductive tissue within a voxel corresponding to the Purkinje candidate node; and
calculating the electrical diffusivity value for each of the Purkinje candidate nodes as a function of the volume fraction of high-speed conductive tissue calculated for the Purkinje candidate node.

40. The non-transitory computer readable medium of claim 39, wherein detecting, from a plurality of nodes of the computational grid, a set of Purkinje candidate nodes based on a distance of each node from the septal endocardium comprises:
calculating a first distance field from the septal endocardium by calculating a discretization of a level-set representation of the endocardial surface over the computational grid; and
for each of the plurality of nodes on the computational grid, selecting the node as a Purkinje candidate node if a value of the first distance field at the node is less than a first threshold.

41. The non-transitory computer readable medium of claim 40, wherein calculating, for each of the Purkinje candidate nodes, a volume fraction of high-speed conductive tissue within a voxel corresponding to the Purkinje candidate node comprises, for each of the Purkinje candidate nodes:
defining a sub-grid of nodes within the voxel corresponding to the Purkinje candidate node;
calculating a second distance field from the septal endocardium by calculating a discretization of the level-set representation of the endocardial surface over the sub-grid defined for the Purkinje candidate node;
for each of the nodes in the sub-grid of nodes within the voxel corresponding to the Purkinje candidate node, classifying the node as high-speed conductive tissue if a value of the second distance field at the node is less than a second threshold and classifying the node as normal tissue if a value of the second distance field at the node is greater than the second threshold; and
calculating the volume fraction of high-speed conductive tissue within the voxel corresponding to the Purkinje candidate node as a number of nodes in the sub-grid of nodes classified as high-speed conductive tissue over a total number of nodes in the sub-grid of nodes.

42. The non-transitory computer readable medium of claim 39, wherein calculating the electrical diffusivity value for each of the Purkinje candidate nodes as a function of the volume fraction of high-speed conductive tissue calculated for the Purkinje candidate node comprises:
calculating the electrical diffusivity value for each of the Purkinje candidate nodes as $D(x)=D_{Purkin}\psi+D_{normal}(1-\psi)$, where $D_{Purkin}$ is an electrical diffusivity value for high-speed conductive tissue, $D_{normal}$ is an electrical diffusivity value for normal tissue, and $\psi$ is the volume fraction of high-speed conductive tissue within the voxel centered at the node x.

43. The non-transitory computer readable medium of claim 42, wherein modeling a Purkinje network of the patient by determining electrical diffusivity values of cardiac tissue in the patient-specific anatomical heart model based on a distance of the cardiac tissue from a septal endocardium in the patient-specific anatomical heart model further comprises:
determining the electrical diffusivity value for each of the plurality of nodes of the computational grid not detected to be Purkinje candidate nodes to be $D_{normal}$.

44. The non-transitory computer readable medium of claim 32, wherein generating a patient-specific anatomical heart model from cardiac image data of a patient comprises:
extracting a multi-component patient-specific heart morphology model from the cardiac image data; and
fusing the multi-component patient-specific heart morphology model into a single heart model and tagging elements of the single heart model according to the multiple components.

45. The non-transitory computer readable medium of claim 44, wherein tagging elements of the single heart model according to the multiple components comprises:
automatically identifying and tagging an endocardium in the single heart model.

46. The non-transitory computer readable medium of claim 36, wherein simulating cardiac electrophysiology for the patient using the cardiac electrophysiology model with the electrical diffusivity values determined to model the electrical conduction system of the heart of the patient comprises:
calculating transmembrane potential variation over time at each of a plurality of nodes within the myocardium in a computational grid corresponding to the patient-specific anatomical heart model by computing a solution of the cardiac electrophysiology model using the electrical diffusivity values determined to model the Purkinje network of the patient for each of the plurality of nodes using a Lattice-Boltzmann method for electrophysiology.

\* \* \* \* \*